(12) United States Patent
Barth et al.

(10) Patent No.: US 6,906,080 B1
(45) Date of Patent: Jun. 14, 2005

(54) PYRAZOLECARBOXYLIC ACID TRICYCLIC DERIVATIVES, PREPARATION AND PHARMACEUTICAL COMPOSITIONS CONTAINING SAME

(75) Inventors: Francis Barth, Saint-Georges-D'Orques (FR); Christian Congy, Saint-Gely-du-Fesc (FR); Serge Martinez, Montpellier (FR); Murielle Rinaldi, Saint-Georges-D'Orques (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/111,765

(22) PCT Filed: Nov. 2, 2000

(86) PCT No.: PCT/FR00/03049

§ 371 (c)(1),
(2), (4) Date: Jul. 30, 2002

(87) PCT Pub. No.: WO01/32663

PCT Pub. Date: May 10, 2001

(30) Foreign Application Priority Data

Nov. 3, 1999 (FR) ............................................. 99 13846

(51) Int. Cl.⁷ .................. C07D 495/04; A61K 31/4162; A61K 31/4439; A61K 31/438
(52) U.S. Cl. ....................... 514/278; 514/322; 514/406; 546/16; 546/199; 548/359.5
(58) Field of Search ....................... 548/359.5; 514/406, 514/322, 278; 546/199, 16

(56) References Cited

U.S. PATENT DOCUMENTS

| | | |
|---|---|---|
| 3,940,418 A | 2/1976 | Hamilton |
| 5,420,141 A | 5/1995 | Boigegrain et al. |
| 5,462,960 A | 10/1995 | Barth et al. |
| 5,624,941 A | 4/1997 | Barth et al. |
| 6,028,084 A | 2/2000 | Barth et al. |

FOREIGN PATENT DOCUMENTS

| | | |
|---|---|---|
| EP | 0477049 | 3/1992 |
| EP | 0568546 | 11/1993 |
| EP | 576357 | 12/1993 |
| EP | 0658546 | 12/1994 |
| WO | WO 96/09304 | 3/1996 |
| WO | WO 97/19063 | 5/1997 |

OTHER PUBLICATIONS

Hamilton, R.W., Journal of Heterocyclic Chemistry, vol. 13, No. 3, pp. 545–553 (1976).
Fravolini, A. et al., Farmaco, Ed. Sci., vol. 33, No. 11, pp. 855–860 (1978).

Primary Examiner—Joseph K. McKane
Assistant Examiner—Rebecca Anderson
(74) Attorney, Agent, or Firm—Kelly Bender

(57) ABSTRACT

The subject of the invention is tricyclic derivatives of pyrazolecarboxylic acid of formula:

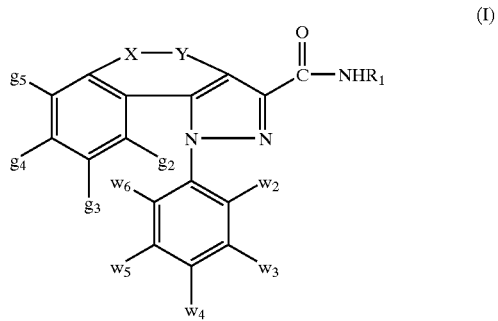

in which $R_1$ represents a $C_3$–$C_{15}$ carboxyl radical or an $NR_2R_3$ group. The invention also relates to the method for preparing the compounds of formula (I), pharmaceutical compositions containing them. The compounds of formula (I) are active on cannabinoid $CB_1$ receptors.

11 Claims, No Drawings

PYRAZOLECARBOXYLIC ACID TRICYCLIC DERIVATIVES, PREPARATION AND PHARMACEUTICAL COMPOSITIONS CONTAINING SAME

This application is a 371 of PCT/FR00/03049 filed Nov. 2, 2000.

The subject of the present invention is compounds which are cannabinoid $CB_1$ receptor antagonists, their preparation, and pharmaceutical compositions containing them. The compounds of the invention are tricyclic derivatives of pyrazolecarboxylic acid.

Patent Applications EP-A-576 357, EP-A-658 546 and WO-97/19063 describe pyrazole derivatives having affinity for the cannabinoid receptors. More particularly, Patent Application EP-A-656 354 claims N-piperidino-5-(4-chlorophenyl)-1-(2,4-dichlorophenyl)-4-methylpyrazole-3-carboxamide and its pharmaceutically acceptable salts which exhibit very good affinity for the cannabinoid $CB_1$ receptors.

International Patent Application WO-96/09304 describes compounds which inhibit cyclooxygenase, more particularly cyclooxygenase-2. These compounds, which are useful in the treatment of inflammation and of inflammatory diseases, correspond to the formula:

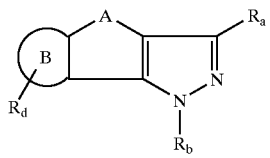

in which:

A, B, $R_a$, $R_b$, $R_d$ have various meanings.

Novel tricyclic derivatives of pyrazolecarboxylic acid have now been found which possess a very good affinity for the cannabinoid $CB_1$ receptors and are useful in therapeutic fields where cannabis is known to be involved.

$\Delta^9$-THC is the main active constituent extracted from *Cannabis sativa* (Tuner, 1985; In Marijuana 84, Ed. Harvey, DY, IRL Press, Oxford).

The effects of cannabinoids are due to an interaction with specific receptors of high affinity present at the central level (Devane et al., Mol. Pharmacol., 1988, 34, 605–613) and peripheral level (Nye et al., Pharmacol. and Experimental Ther., 1985, 234, 784–791; Kaminski et al., 1992, Mol. Pharmacol., 42, 736–742; Munro et al., Nature, 1993, 365, 61–65).

The characterization of the receptors has been made possible by the development of synthetic ligands for the cannabinoid receptors such as the agonists WIN 55212-2 (J. Pharmacol. Exp. Ther., 1993, 264, 1352–1363) or CP 55,940 (J. Pharmacol. Exp. Ther., 1988, 247, 1046–1051).

The subject of the present invention is compounds of formula:

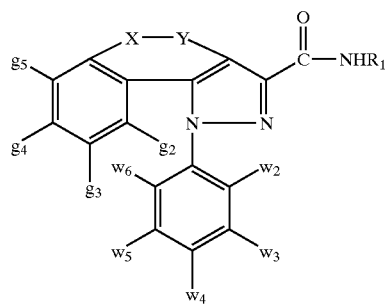

in which:

X—Y— represents a group chosen from —$(CH_2)_n$—$CH_2$—, —$CH_2$—$S(O)_p$— or —$S(O)_p$—$CH_2$—;

n is equal to 1 or 2;

p is equal to zero, 1 or 2;

$g_2$, $g_3$, $g_4$, $g_5$, $w_2$, $w_3$, $w_4$, $w_5$, $w_6$ are identical or different and each independently represent hydrogen, a halogen, a trifluoromethyl, a $(C_1$–$C_4)$alkyl, a $(C_1$–$C_4)$alkoxy, a $(C_1$–$C_4)$alkylthio, a nitro; at least one of the substituents $w_2$, $w_3$, $w_4$, $w_5$, $w_6$ being different from hydrogen;

$R_1$ represents a nonaromatic $C_3$–$C_{15}$ carbocyclic radical which is unsubstituted or substituted one or several times with a $(C_1$–$C_4)$alkyl, or an $NR_2R_3$ group;

$R_2$ and $R_3$ each separately represent hydrogen or a $(C_1$–$C_6)$alkyl, or $R_2$ or $R_3$, together with the nitrogen atom to which they are attached, constitute a saturated or unsaturated 5- to 10-membered heterocyclic radical which is unsubstituted or substituted one or several times with a $(C_1$–$C_4)$alkyl;

as well as their salts and their solvates.

The expression alkyl is understood to mean straight or branched alkyls. The methyl, ethyl, propyl and isopropyl groups are preferred.

The expression saturated or unsaturated 5- to 10-membered heterocyclic radical is understood to mean a nonaromatic mono- or dicyclic heterocyclic radical which is condensed or bridged, and which may contain a second heteroatom. These radicals comprise in particular the following radicals: 1-pyrrolidinyl, 1-piperidinyl, 1-hexahydroazepinyl, 4-morpholinyl, 8-azaspiro[4.5]dec-8-yl, bicyclo[2.2.1]heptan-2-yl.

The expression nonaromatic $C_3$–$C_{15}$ carbocyclic radical is understood to mean a saturated mono- or polycyclic radical which is condensed, bridged or a spiro compound, a saturated condensed or bridged radical being preferred. These radicals comprise in particular the following radicals: cyclopentyl, cyclohexyl or adamantyl or fenchyl.

The expression halogen is understood to mean a chlorine, bromine, fluorine or iodine atom.

The possible salts of the compounds of formula (I) comprise the pharmaceutically acceptable acid addition salts such as the hydrochloride, hydrobromide, sulfate, hydrogen sulfate, dihydrogen phosphate, methanesulfonate, methyl sulfate, maleate, oxalate, fumarate, naphthalenesulfonate, glyconate, gluconate, citrate, isethionate, para-toluenesulfonate, methylenesulfonate, benzenesulfonate or succinate.

The subject of the present invention is most particularly compounds of formula:

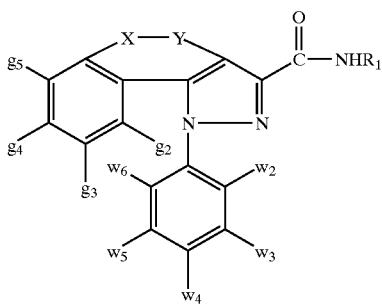

in which
- X—Y— represents a group chosen from —(CH$_2$)$_n$—CH$_2$—, —CH$_2$—S(O)$_p$— or —S(O)$_p$—CH$_2$—;
- n is equal to 1 or 2;
- p is equal to zero, 1 or 2;
- g$_2$, g$_3$, g$_4$, g$_5$, w$_2$, w$_3$, w$_4$, w$_5$, w$_6$ are identical or different and each independently represent hydrogen, a halogen, a trifluoromethyl, a (C$_1$–C$_3$)alkyl, a (C$_1$–C$_3$)alkoxy, a (C$_1$–C$_3$)alkylthio, a nitro; at least one of the substituents w$_2$, w$_3$, w$_4$, w$_5$, w$_6$ being different from hydrogen;
- R$_1$ represents a nonaromatic C$_3$–C$_{15}$ carbocyclic radical which is unsubstituted or substituted one or several times with a (C$_1$–C$_4$)alkyl, or an NR$_2$R$_3$ group;
- R$_2$ and R$_3$ each separately represent hydrogen or a (C$_1$–C$_6$)alkyl, or R$_2$ or R$_3$, together with the nitrogen atom to which they are attached, constitute a saturated or unsaturated 5- to 10-membered heterocyclic radical which is unsubstituted or substituted one or several times with a (C$_1$–C$_4$)alkyl;

as well as their salts and their solvates.

Among the compounds of formula (I), those in which g$_2$, g$_3$, g$_5$, w$_3$, w$_5$, w$_6$ represent hydrogen and g$_4$, w$_2$ and w$_4$ have one of the values defined above for the compounds of formula (I), except hydrogen, are preferred. More particularly, the compounds of formula (I) in which w$_2$ and w$_4$ represent chlorine and g$_4$ represents chlorine or bromine are preferred.

Among the compounds of formula (I), the compounds in which R$_1$ represents a nonaromatic C$_3$–C$_{15}$ carbocyclic radical which is unsubstituted or substituted one or several times with a (C$_1$–C$_4$)alkyl are distinguished.

Among the compounds of formula (I), the compounds in which R$_1$ represents NR$_2$R$_3$ are also distinguished, R$_2$ and R$_3$ constituting, with the nitrogen atom to which they are attached, a saturated 5- to 10-membered heterocyclic radical which is unsubstituted or substituted one or several times with a (C$_1$–C$_4$)alkyl.

Among the compounds of formula (I), those in which X—Y represents a group —(CH$_2$)$_n$—CH$_2$—, and those in which X—Y represents a group —CH$_2$—S(O)$_p$— or a group —S(O)$_p$—CH$_2$—, are distinguished. The compounds of formula (I) in which X—Y represents —CH$_2$—CH$_2$—, —CH$_2$—CH$_2$—CH$_2$— or —CH$_2$—S— are preferred.

In the present description, the following abbreviations are used:
- ether: diethyl ether
- iso ether: diisopropyl ether
- EtOH: ethanol
- MeOH: methanol
- DCM: dichloromethane
- AcOEt: ethyl acetate
- LiHMDS: lithium salt of hexamethyldisilazane
- (CO$_2$Et)$_2$: ethyl oxalate
- APTS: para-toluenesulfonic acid
- PPA: polyphosphoric acid
- DIBAL: diisobutylaluminum hydride
- AcOH: acetic acid
- RT: room temperature
- m.p.: melting point
- b.p.: boiling point
- p: pressure
- NMR: nuclear magnetic resonance. The NMR spectra are recorded at 200 MHz in DMSO-d6
- s: singlet; d: doublet; t: triplet, m: unresolved complex.

The subject of the present invention is also a method for preparing a compound according to the invention, its salts and its solvates. This method is characterized in that a functional derivative of an acid of formula:

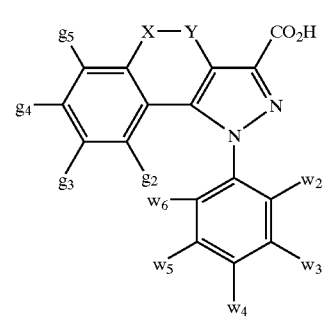

in which —X—Y— and g$_2$, g$_3$, g$_4$, g$_5$, w$_2$, w$_3$, w$_4$, w$_5$, w$_6$ are as defined above for (I), is treated with a compound of formula NH$_2$R$_1$ (III), in which R$_1$ is as defined above for (I).

The reaction is carried out in basic medium, for example in the presence of triethylamine in a solvent such as dichloromethane or tetrahydrofuran.

As functional derivative of the acid (II), it is possible to use the acid chloride, the anhydride, a mixed anhydride, a C$_1$–C$_4$ alkyl ester in which the alkyl is straight or branched, an activated ester, for example p-nitrophenyl ester, or the free acid opportunely activated, for example, with N,N-dicyclohexylcarbodiimide or with benzotriazolyl-N-oxotris(dimethylamino)phosphonium hexafluorophosphate (BOP).

Thus, by the method according to the invention, it is possible to react the chloride of the acid of formula (II) obtained by reacting thionyl chloride with the acid of formula (II) in an inert solvent such as benzene or toluene or a chlorinated solvent (dichloromethane, dichloroethane, chloroform for example), an ether (tetrahydrofuran, dioxane for example), or an amide (N,N-dimethylformamide for example) under an inert atmosphere, at a temperature of between 0° C. and the reflux temperature of the solvent.

A variant to the procedure consists in preparing the mixed anhydride of the acid of formula (II) by reacting ethyl chloroformate with the acid of formula (II), in the presence of a base such as triethylamine.

A few acids of formula (II) have been described in the literature.

The publication by Fravolini et al., Farmaco ed. Sci., 1978, 33 (11), 855–865 describes compounds of formula:

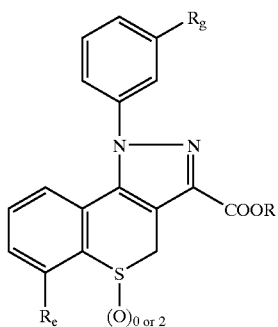

which are intermediates for preparing compounds tested for anti-inflammatory, analgesic and cardiovascular activities.

Among the compounds described, the following values for the substituents are found:

$R_e$=Ht and $R_g$=F;
$R_e$=H and $R_g$=CF$_3$.

The publication by Hamilton in J. Het. Chem., 1976, 13 (3), 545–553 and U.S. Pat. No. 3,940,418 describe compounds of formula:

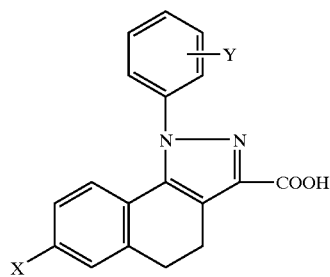

Among these compounds, the following substituents are described:

Y=p–Cl and X=H or X=OCH$_3$.

Apart from the abovementioned compounds, the initial acids (II) are novel and constitute another aspect of the present invention; their functional derivatives are also novel, in particular their acid chlorides and their $C_1$–$C_4$ alkyl esters.

Thus, the subject of the present invention is also the acids of formula:

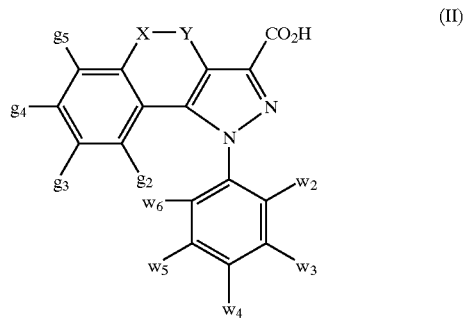

in which $g_2$, $g_3$, $g_4$, $g_5$, $w_2$, $w_3$, $w_4$, $w_5$, $w_6$ are as defined for (I) in claim 1 and their functional derivatives, provided that:

when X—Y is —S—CH$_2$ or —SO$_2$—CH$_2$—, and $w_5$ represents a fluorine or a trifluoromethyl, $g_2$, $g_3$, $g_4$, $g_5$, $w_2$, $w_3$, $w_4$, $w_5$, $w_6$ do not simultaneously represent hydrogen;

when X—Y is —CH$_2$—CH$_2$—, $w_4$ represents a chlorine and $g_4$ represents hydrogen or a methoxy, $g_2$, $g_3$, $g_5$, $w_2$, $w_3$, $w_5$, $w_6$ do not simultaneously represent hydrogen.

The acid of formula (II) is obtained according to the reaction scheme below:

Scheme 1

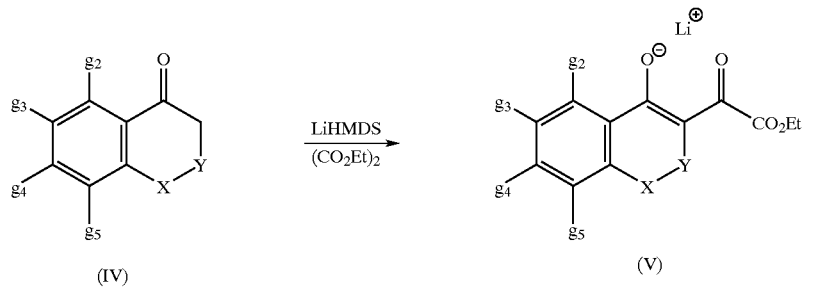

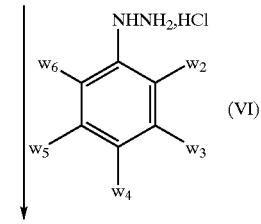

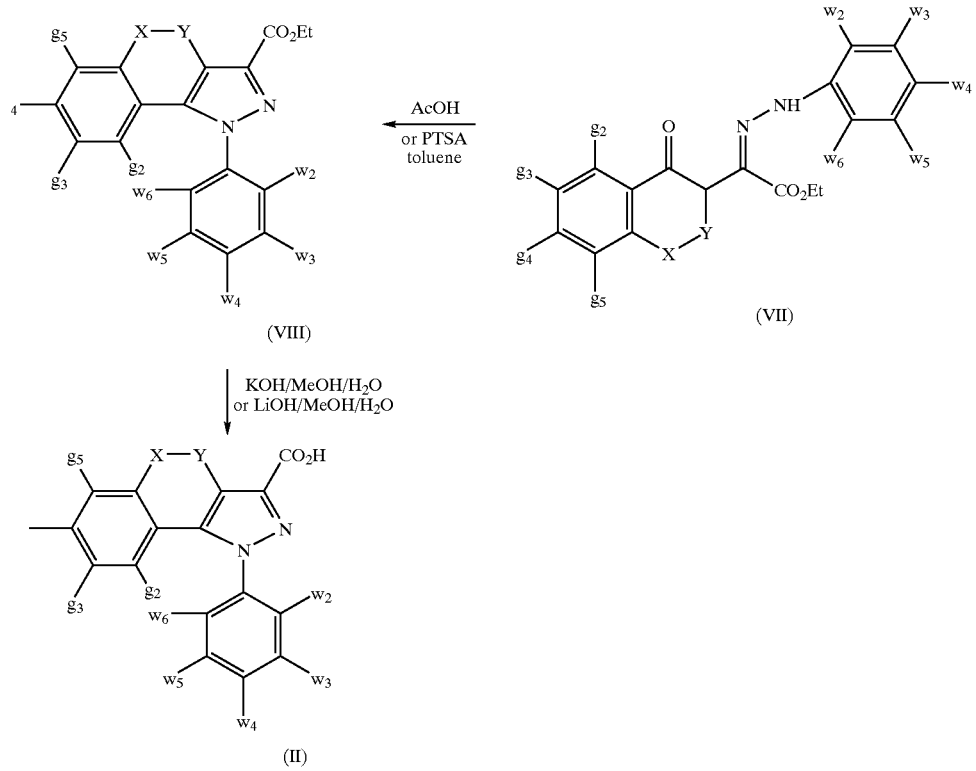

The thiochroman-4-ones (IV, —X—Y—=—S—CH$_2$—) and the isothiochroman-4-ones (IV, —X—Y—=—CH$_2$—S—) are prepared according to the methods described in WO-96/09304. In particular, 7-chloroisothiochroman-4-one, 7-fluoroisothiochroman-4-one as well as 7-chlorothiochroman-4-one are described in this International Application WO-96/09304.

When —X—Y— represents respectively —CH$_2$—SO—, CH$_2$—SO$_2$— or respectively —SO—CH$_2$—, SO$_2$CH$_2$—, a compound of formula (VIII) is prepared in which —X—Y— represents respectively —CH$_2$—S— or respectively —S—CH$_2$ and there is reacted an oxidizing agent such as meta-chloroperbenzoic acid, either in equimolar quantity in order to obtain a sulfoxide, or in double quantity in order to obtain a sulfone.

The tetralones of formula (IV) in which —X—Y— represents —CH$_2$—CH$_2$— are known or prepared by known methods as described in Synthetic Communications, 1991, 21, 981–987.

The benzosuberones of formula (IV) in which —X—Y— represents —(CH$_2$)$_2$—CH$_2$— are known or prepared according to J. Med. Chem., 1991, 37, 3482–3491 and J. Org. Chem., 1962, 27, 7076.

The lithium salt of formula (V) is prepared by the action of a lithium-containing base such as hexamethyldisilazane and then of ethyl oxalate.

By the action of phenylhydrazine hydrochloride (VI), the compound of formula (VII) is prepared; the latter is then cyclized by heating in the presence of acetic acid or in the presence of para-toluenesulfonic acid in toluene. A saponification is then carried out according to conventional methods, for example in the presence of potassium hydroxide or lithium hydroxide in methanol, in order to obtain the expected acid of formula (II).

The starting amine-containing derivatives of formula (III) are known or prepared by known methods, in particular those described in EP-0658546. Thus, 8-azaspiro[4.5]dec-8-ylamine is prepared from 8-azaspiro[4.5]decane, itself prepared according to J. Med. Chem., 1964, 7, 784–786 or Bull. Soc. Chem. Fr., 1964, 2572–2579. (1S)-Endo-1,3,3-trimethylbicyclo[2.2.1]heptan-2-ylamine is prepared according to J. Am. Chem. Soc., 1951, 73, 3360 or according to J. Med. Chem., 1991, 34, 1003. 4,4-Dimethylpiperidin-1-ylamine is prepared according to J. Med. Pharm. Chem., 1962, 5, 815.

The compound of formula (I) obtained by the method according to the invention is isolated, in the form of a free base or of a salt or of a solvate, according to conventional techniques.

The compound of formula (I) may be isolated in the form of one of its salts, for example the hydrochloride or oxalate; in this case, the free base may be prepared by neutralizing said salt with an inorganic or organic base, such as sodium or ammonium hydroxide, triethylamine or an alkali metal carbonate or bicarbonate such as sodium or potassium carbonate or bicarbonate, and converted to another salt such as the methanesulfonate, fumarate or 2-naphthalenesulfonate.

When the compound of formula (I) is obtained in the form of a free base, the salification is carried out by treating with the chosen acid in an organic solvent. By treating the free base, dissolved for example in an ether such as diethyl ether or in acetone, with a solution of the acid in the same solvent, the corresponding salt is obtained, which is isolated according to conventional techniques.

The compounds of formula (I) possess a very good affinity in vitro for the cannabinoid $CB_1$ receptors, under the experimental conditions described by Devane et al., Mol. Pharmacol., 1988, 34, 605–613.

More particularly, the compounds of the present invention, as they are or in the form of one of their pharmaceutically acceptable salts, are potent and selective cannabinoid $CB_1$ receptor antagonists having a Ki of less than $5 \times 10^{-7}$M. They are at least ten times more active on the $CB_1$ receptors than on the $CB_2$ receptors.

Moreover, their antagonist nature has been demonstrated by the results in the adenylate-cyclase inhibition models as described in M. Rinaldi-Carmona et al., J. Pharmacol. Exp. Ther., 1996, 278, 871–878.

The toxicity of the compounds (I) is compatible with their use as a medicament.

According to another of its aspects, the present invention relates to the use of the compounds of formula (I), or of one of their pharmaceutically acceptable salts and solvates, for the preparation of medicaments intended for treating diseases involving the cannabinoid $CB_1$ receptors.

For example and without limitation, the compounds of formula (I) are useful as psychotropic medicaments, in particular for the treatment of anxiety disorders, mood disorders, delirium disorders, psychotic disorders in general, for the treatment of schizophrenia, depression, as well as for the treatment of disorders related to the use of psychotropic substances, in particular in the case of substance abuse and/or dependency on a substance, including alcohol dependency.

The compounds (I) according to the invention may be used as medicaments for the treatment of neuropathies, migraine, stress, diseases of psychosomatic origin, epilepsy, movement disorders, in particular dyskinesia or Parkinson's disease.

The compounds (I) according to the invention may also be used as medicaments in the treatment of memory disorders, cognitive disorders, in particular in the treatment of senile dementia, Alzheimer's disease, as well as in the treatment of attention or vigilance disorders and as neuroprotectants.

The compounds (I) according to the invention may be used as medicaments in appetite disorders, palatability disorders (for sugars, carbohydrates, drugs, alcohols or any appetizing substance) and/or alimentary canal disorders, in particular as anorexigen or for the treatment of obesity or bulimia as well as for the treatment of type II diabetes or non-insulin-dependent diabetes and in smoking cessation. Further-more, the compounds of formula (I) according to the invention may be used as medicaments in gastrointestinal disorders, vomiting, vesical and urinary disorders, cardiovascular disorders, fertility disorders, inflammatory phenomena, infectious diseases and as medicaments for anticancer chemotherapy.

The compounds according to the present invention may also be useful in the treatment of neuroinflammatory pathologies, in particular diseases causing demyelination such as multiple sclerosis or Guillain-Barré syndrome, as well as viral encephalitis, stroke, cranial trauma, for example.

According to the present invention, the compounds of formula (I) are most particularly useful for the treatment of psychotic disorders, in particular schizophrenia; for the treatment of appetite disorders and obesity, for smoking cessation and for the treatment of memory and cognitive disorders.

According to one of its aspects, the present invention relates to the use of a compound of formula (I) for the treatment of the disorders and diseases indicated above.

According to another of its aspects, the present invention also relates to the use of the compounds of formula (I), as they are or in radiolabeled form, as pharmacological tools in humans or in animals, for the detection and labeling of $CB_1$ receptors.

The compounds according to the invention are generally administered as a dosage unit.

Said dosage units are preferably formulated in pharmaceutical compositions in which the active ingredient is mixed with a pharmaceutical excipient.

Thus, according to another of its aspects, the present invention relates to pharmaceutical compositions containing, as active ingredient, a compound of formula (I), one of its pharmaceutically acceptable salts or one of their solvates.

The compounds of formula (I) above and their pharmaceutically acceptable salts or solvates may be used at daily doses of 0.01 to 100 mg per kg of body weight of the mammal to be treated, preferably at daily doses of 0.1 to 50 mg/kg. In human beings, the dose may vary preferably from 0.5 to 4 000 mg per day, more particularly from 2 to 1 000 mg per day according to the age of the subject to be treated or the type of treatment, namely prophylactic or curative.

In the pharmaceutical compositions of the present invention for oral, sublingual, inhaled, subcutaneous, intramuscular, intravenous, transdermal, local or rectal administration, the active ingredient may be administered in unit form for administration, as a mixture with conventional pharmaceutical carriers, to animals and to human beings. The appropriate unit forms for administration comprise the forms for administration by the oral route such as tablets, gelatin capsules, powders, granules and oral solutions or suspensions, the forms for sublingual or buccal administration, aerosols, the forms for topical administration, implants, the forms for subcutaneous, intramuscular, intravenous, intranasal or intraocular administration and the forms for rectal administration.

In the pharmaceutical compositions of the present invention, the active ingredient is generally formulated as dosage units containing from 0.1 to 1 000 mg, advantageously from 0.5 to 500 mg, preferably from 1 to 200 mg of said active ingredient per dosage unit for daily administration.

When a solid composition in tablet form is prepared, it is possible to add to the micronized or nonmicronized active ingredient a wetting agent such as sodium lauryl sulfate and the whole is mixed with a pharmaceutical vehicle such as silica, gelatin, starch, lactose, magnesium stearate, talc, gum arabic or the like. It is possible to coat the tablets with sucrose, with various polymers or with other appropriate materials or alternatively to treat them such that they have a prolonged or delayed activity and that they continuously release a predetermined quantity of active ingredient.

A preparation in the form of gelatin capsules is obtained by mixing the active ingredient with a diluent such a glycol or a glycerol ester and by incorporating the mixture obtained into soft or hard gelatin capsules.

A preparation in syrup or elixir form may contain the active ingredient together with a sweetener, preferably a calorie-free sweetener, methylparaben and propylparaben as antiseptics, as well as a flavoring agent and an appropriate coloring.

The water-dispersible powders or granules may contain the active ingredient in the form of a mixture with dispersing agents, wetting agents or suspending agents, such as polyvinylpyrrolidone, and with sweeteners or flavor correctors.

For rectal administration, suppositories are used which are prepared with binders which melt at rectal temperature, for example cocoa butter or polyethylene glycols.

For parenteral, intranasal or intraocular administration, aqueous suspensions, isotonic saline solutions or sterile and injectable solutions are used which contain pharmacologically compatible dispersing agents and/or solubilizing agents, for example propylene glycol or polyethylene glycol.

Thus, to prepare an aqueous solution which can be injected by the intravenous route, it is possible to use a cosolvent such as, for example, an alcohol such as ethanol or a glycol such as polyethylene glycol or propylene glycol, and a hydrophilic surfactant such as Tween® 80. To prepare an oily solution which can be injected by the intramuscular route, the active ingredient may be solubilized with a triglyceride or a glycerol ester.

For local administration, creams, ointments or gels may be used.

For transdermal administration, it is possible to use patches in multilaminate form or containing reservoirs in which the active ingredient may be in alcoholic solution.

For administration by inhalation, an aerosol is used containing, for example, sorbitan trioleate or oleic acid as well as trichlorofluoromethane, dichlorofluoromethane, dichlorotetrafluoroethane or any other biologically compatible propellant gas; it is also possible to use a system containing the active ingredient alone or combined with an excipient, in powdered form.

The active ingredient-may also be formulated in the form of microcapsules or microspheres, optionally with one or more carriers or additives.

The active ingredient may also be provided in the form of a complex with a cyclodextrin, for example α-, β- or γ-cyclodextrin, 2-hydroxypropyl-β-cyclodextrin or methyl-α-cyclodextrin.

Among the prolonged-release forms useful in the case of chronic treatments, implants may be used. They may be prepared in the form of an oily suspension or in the form of a suspension of microspheres in an isotonic medium.

Preparation 1

7-Chloro-1-(2,4-dichlorophenyl)-1,5-dihydroisothiochromeno[4,3-c]pyrazole-3-carboxylic Acid II: $g_4=w_2=w_4=Cl$, X—Y=$CH_2$—S.

A) 7-Chloroisothiochroman-4-one.

This compound is prepared according to the procedure described in International Patent Application WO 96/09304.

B) Ethyl ester of the lithium salt of (7-chloro-4-oxido-1H-isothiochromen-3-yl)oxoacetic acid.

A solution of 3.44 g of lithium salt of hexamethyldisilazane in 85 ml of diethyl ether is cooled to −60° C. and a solution of 3.71 g of the compound obtained in the preceding step in 60 ml of diethyl ether is added dropwise and under a nitrogen atmosphere. The temperature of the reaction mixture is allowed to rise to −30° C., 2.8 ml of diethyl oxalate are added all at once and the mixture is left for 18 hours, with stirring, at RT. The precipitate formed is drained, it is washed with diethyl ether and dried under vacuum. 4.58 g of the expected product are obtained, which product is used as it is in the next step.

C) Ethyl ester of (7-chloro-4-oxoisothiochroman-3-yl)(2,4-dichlorophenylhydrazono)acetic acid.

1.75 g of 2,4-dichlorophenylhydrazine hydrochloride are added to a suspension of 2.50 g of the compound obtained in the preceding step in 35 ml of EtOH, at RT, and the mixture is left for 4 hours, with stirring, at RT. The precipitate formed is drained, it is washed with EtOH and dried under vacuum in order to obtain a first crop. The draining and washing liquors are concentrated under vacuum by half and left for 16 hours, with stirring, at RT. The precipitate formed is drained, it is washed with EtOH and dried under vacuum in order to obtain a second crop. 1.18 g of the expected product are obtained in total, m.p.=170° C.

D) Ethyl ester of 7-chloro-1-(2,4-dichlorophenyl)-1,5-dihydroisothiochromeno-[4,3-c]pyrazole-3-carboxylic acid.

A mixture of 2.09 g of the compound obtained in the preceding step and 55 ml of acetic acid is heated under reflux for 18 hours, and then it is left for 56 hours, with stirring, at RT. The reaction mixture is poured into 500 ml of ice-cold water, the precipitate formed is drained, it is washed with water and dried under vacuum. 1.93 g of the expected product are obtained, m.p.=95° C.

E) 7-Chloro-1-(2,4-dichlorophenyl)-1,5-dihydroisothiochromeno[4,3-c]pyrazole-3-carboxylic acid.

A solution of 0.31 g of KOH in 10 ml of water is added to a solution of 0.91 g of the compound obtained in the preceding step in 30 ml of MeOH, and then the mixture is heated under reflux for 3 hours. The reaction mixture is poured over a solution of 10 ml of 5% $H_2SO_4$ and 300 ml of ice-cold water, extracted with DCM, the organic phase is washed with water, with a saturated NaCl solution, dried over $MgSO_4$ and the solvent is evaporated under vacuum. 0.7 g of the expected product is obtained, m.p.=262° C.

NMR: 4.10 ppm: s: 2H; 6.60 ppm : d : 1H; 7.25 ppm : d : 1H; 7.65–8.10 : m : 4H.

Preparation 2

7-Chloro-1-(2,4-dichlorophenyl)-4,4-dioxo-4,5-dihydro-1H-4$\lambda^6$-isothiochromeno[4,3-c]pyrazole-3-carboxylic Acid II: $g_4=w_2=w_4=Cl$, X—Y=$CH_2$—$SO_2$.

A) Ethyl ester of 7-chloro-1-(2,4-dichlorophenyl)-4,4-dioxo-4,5-dihydro-1H-4$\lambda^6$-isothiochromeno[4,3-c]pyrazole-3-carboxylic acid.

2.96 g of meta-chloroperbenzoic acid are dissolved in 45 ml of DCM and this solution is poured dropwise over 1 hour, at a temperature of between 0° C. and 5° C., over a solution containing 2.51 g of the ester obtained in PREPARATION 1, step D, in solution in 80 ml of DCM. After 3 hours, with stirring, at room temperature, 250 ml of a 10% $Na_2CO_3$ solution are added and then the mixture is left for 10 minutes, with stirring. It is extracted with DCM, and then washed with a 10% $Na_2CO_3$ solution, with an NaCl solution, and then twice with a saturated aqueous NaCl solution. 2.58 g of the expected compound are obtained.

B) 7-Chloro-1-(2,4-dichlorophenyl)-4,4-dioxo-4,5-dihydro-1H-4×6-isothiochromeno-[4,3-c]pyrazole-3-carboxylic acid.

505 mg of ester obtained in the preceding step are dissolved in 15 ml of methanol, and 133 mg of LiOH and 1 ml of water are added. After 2 hours, with stirring, at RT, the methanol is concentrated under vacuum and the residue is taken up in 10 ml of ice-cold water. The mixture is acidified to pH=2 with 1N HCl and then the precipitate obtained is filtered, it is washed with water and it is dried under vacuum to give 0.457 g of the expected compound in the form of an amorphous solid.

NMR: 5.10 ppm : AB system : 2H; 6.80 ppm : d : 1H; 7.55 ppm : dd : 1H; 7.80–8.15 ppm : m : 4H.

Preparation 3

7-Chloro-1-(2,4-dichlorophenyl)-4-oxo-4,5-dihydro-1H-4$\lambda^4$-isothiochromeno[4,3-c]pyrazole-3-carboxylic Acid II: $g_4$=$w_2$=$w_4$=Cl, X—Y=$CH_2$—SO.

A) Ethyl ester of 7-chloro-1-(2,4-dichlorophenyl)-4-oxo-4,5-dihydro-1H-4$\lambda^4$-isothiochromeno[4,3-c]pyrazole-3-carboxylic acid.

A solution of 0.86 g of meta-chloroperbenzoic acid is prepared in 100 ml of DCM and then it is added dropwise to a solution at 0° C. containing 1.47 g of ester obtained in PREPARATION 1, step D in solution in 100 ml of DCM. After stirring for 3 and a half hours, 50 ml of a 5% $Na_2CO_3$ solution are added and then the mixture is stirred for 15 minutes. It is extracted with DCM and then washed with a saturated solution and then a dilute solution of NaCl. After evaporating the solvents and drying, the residue is chromatographed on silica, eluting with a toluene/AcOEt (90/10; v/v) mixture. 0.99 g of the expected compound is obtained.

B) 7-Chloro-1-(2,4-dichlorophenyl)-4-oxo-4,5-dihydro-1H-4$\lambda^4$-isothiochromeno[4,3-c]pyrazole-3-carboxylic acid.

A solution containing 0.265 g of lithium hydroxide in 3 ml of water is added to a solution of 960 mg of ester obtained in the preceding step in 40 ml of methanol. After stirring for 2 hours, the methanol is concentrated to dryness, the residue is taken up with ice-cold water and then the mixture is acidified to pH=2 by addition of 1N HCl. The white precipitate obtained is filtered, washed with water and then dried under vacuum. 0.7 g of the expected compound is obtained in the form of an amorphous solid.

NMR: 5.75–6.00 ppm : m : 1H; 6.50–6.70 ppm : m : 1H; 7.20–8.10 ppm : m : 6H.

Preparation 4

7-Chloro-1-(2,4-dichlorophenyl)-4,5-dihydro-1H-benzo[g]indazole-3-carboxylic Acid II: $g_4$=$w_2$=$w_4$=Cl, X-Y=—$(CH_2)_2$—.

A) 6-Chloro-3,4-dihydro-2H-naphthalen-1-one.

This compound is prepared according to Synthetic Commun., 1991, 21 (8 and 9), 981–987.

B) Ethyl ester of the lithium salt of (6-chloro-1-oxido-3,4-dihydronaphthalen-2-yl)oxoacetic acid.

6.34 g of lithium salt of hexamethyl-disilazane are placed in 100 ml of anhydrous ether, at −60° C., under nitrogen, and then a solution containing 6.2 g of the compound of step A in 50 ml of ether is poured in dropwise. The reaction medium is kept at about 30° C. for 30 minutes and then 5.15 ml of ethyl oxalate are added. After stirring overnight, the precipitate obtained is filtered, rinsed with ether and dried under vacuum to give 8.2 g of the expected compound.

C) Ethyl ester of 6-chloro-1-oxo-1,2,3,4-tetrahydronaphthalen-2-yl)[2,4-dichlorophenylhydrazino]acetic acid.

5.23 mg of the lithium salt obtained in the preceding step are placed in 50 ml of ethanol and 3.9 g of 2,4-dichlorophenylhydrazine hydrochloride are added. After 6 hours at RT, with stirring, the precipitate formed is filtered, rinsed with ethanol and dried under vacuum to give 3.8 g of the expected compound.

D) Ethyl ester of 7-chloro-1-(2,4-dichloro-phenyl)-4,5-dihydro-1H-benzo[g]indazole-3-carboxylic acid.

A mixture containing 3.8 g of the compound obtained in the preceding step and 50 ml of acetic acid is heated under reflux for 11 hours. 20 ml of ice-cold water are added and then the precipitate obtained is filtered, rinsed with ice-cold water and dried under vacuum. The residue is chromatographed on silica, eluting with a cyclohexane/AcOEt (90/10; v/v) mixture and 2 g of the expected compound are obtained.

E) 7-Chloro-1-(2,4-dichlorophenyl)-4,5-dihydro-1H-benzo[g]indazole-3-carboxylic acid.

2 g of ester obtained in the preceding step are placed in 30 ml of MeOH, 0.66 g of potassium hydroxide in 4.2 ml of water are added and then the mixture is heated for 2 hours under reflux and left overnight at RT.

The mixture is concentrated under vacuum, the residue is taken up in ice-cold water, acidified to pH=1 by addition of 1N HCl and then extracted with AcOEt and washed with a saturated NaCl solution. 1.8 g of the expected compound are obtained. m.p.=237° C.

NMR: 2.75–3.00 ppm : m : 4H; 6.35 ppm : d : 1H; 7.10 ppm : dd : 1H; 7.40: d : 1H; 7.60–7.75 ppm : m : 2H; 7.90: d : 1H.

Preparation 5

7-Trifluoromethyl-1-(2,4-dichlorophenyl)-4,5-dihydro-1H-benzo[g]indazole-3-carboxylic Acid II: $g_4$=$CF_3$, $w_2$=$w_4$=Cl, X—Y=—$(CH_2)_2$—.

A) (3-Trifluoromethyl)phenyltributyltin.

5.62 g of magnesium are placed in 42 ml of ether, 31 ml of (3-trifluoromethyl)bromobenzene are added and then the mixture is heated for 8 hours under reflux and left for 1 hour at RT. 46.3 ml of tributyltin chloride diluted in 46 ml of ether are added to this solution. After 2 hours at RT, the mixture is heated for 6 hours under reflux and then hydrolyzed by addition of 140 ml of water, cooling to a temperature of between 0° C. and 5° C. After distillation under vacuum, 65 g of the expected compound are obtained.

B) Methyl ester of 4-(3-trifluoromethyl-phenyl)but-2-enoic acid.

0.765 g of bis(triphenylphosphine)palladium(II) chloride in suspension in 180 ml of THF is introduced into a three-necked flask and then 2.58 ml of DIBAL (1M in toluene) are added dropwise and the mixture is kept stirring for 45 minutes at RT. A mixture containing 65 g of the compound prepared in the preceding step and 27 g of methyl ester of 4-bromobut-2-enoic acid in 100 ml of THF is then added. The reaction mixture is heated under reflux for 16 hours and then filtered on Celite® and the filtrate is concentrated to dryness. The residue is chromatographed on silica, eluting with a cyclohexane/AcOEt (90/10; v/v) mixture. 44 g of the expected compound are obtained.

C) Methyl ester of 4-(3-trifluoromethylphenyl)-butanoic acid.

26 g of the compound obtained in the preceding step and 1.8 g of 10% Pd/C in 500 ml of ethanol are stirred for 6 days at a hydrogen pressure of 4 bar. After evaporation of the solvents and drying, the residue is chromatographed on silica, eluting with a cyclohexane/AcOEt (90/10; v/v) mixture. 15.83 g of the expected compound are obtained.

D) 4-(3-Trifluoromethylphenyl)butanoic acid.

15.83 g of ester obtained in the preceding step are diluted in 150 ml of THF and a suspension of 5.37 g of LiOH in 10.7 ml of water is added. After heating overnight under reflux, the THF is concentrated and then the residue is taken up in water at a temperature of less than 5° C. and acidified to pH=2 with 1N HCl. The mixture is extracted with ether, separated by settling and washed with water to give 14 g of the expected compound.

E) 6-(Trifluoromethyl)-3,4-dihydro-2H-naphthalen-1-one.

9.5 g of acid obtained in the preceding step and 270 g of PPA are mixed and heated at 65° C. for 2 hours. 500 ml of water are added and then, after cooling, the mixture is extracted with AcOEt and separated by settling. The mixture is washed with water, a 5% $Na_2CO_3$ solution, a saturated NaCl solution and then dried and the residue is chromatographed on silica, eluting with a cyclohexane/AcOEt (94/6; v/v) mixture. 1.6 g of the expected compound are obtained.

F) 7-Trifluoromethyl-1-(2,4-dichlorophenyl)-4,5-dihydro-1H-benzo[g]indazole-3-carboxylic acid.

The procedure is then carried out as described in PREPARATION 1 to give the expected compound. m.p.=245° C.

NMR: 2.95–3.25 ppm : m : 4H; 6.75 ppm : d : 1H; 7.55 ppm : d : 1H; 7.75–7.95 ppm : m : 3H; 8.10: d: 1H.

Preparation 6

1–2,4-Dichlorophenyl)-1,4,5,6-tetrahydro-1,2-diazabenzo[e]azulene-3-carboxylic Acid II: $g_4$=H, $w_2$=$w_4$=Cl, X—Y=—(CH$_2$)$_3$—.

Benzosuberone (6,7,8,9-tetrahydrobenzocyclo-hepten-5-one) is a commercial product.

A) Ethyl ester of the lithium salt of (5-oxido-8,9-dihydro-7-benzocyclohepten-6-yl)oxoacetic acid.

5.74 g of lithium salt of hexamethyl-disilazane in suspension are introduced into 90 ml of ether under nitrogen and the mixture is cooled to a temperature of −60° C. and then a solution containing 5 g of benzosuberone in 60 ml of ether is added over 15 minutes. The temperature is allowed to rise to −30° C. and then 4.7 ml of ethyl oxalate are rapidly added. After returning to RT, the mixture is kept stirring for 4 hours and then the precipitate formed is filtered, rinsed with ether and dried under vacuum to give 8.1 g of the expected compound.

B) Ethyl ester of 5-oxo-6,7,8,9-tetrahydro-5H-benzocyclohepten-6-yl)(2,4-dichlorophenyl-hydrazono)acetic acid.

8.1 g of the lithium salt obtained in the preceding step in 100 ml of ethanol and 6.5 g of 2,4-dihydrophenylhydrazine hydrochloride are mixed. After 4 hours, with stirring, at RT, the solid obtained is filtered, rinsed with ethanol and dried under vacuum to give 5.75 g of the expected compound.

C) Ethyl ester of 1-(2,4-dichlorophenyl)-1,4,5,6-tetrahydro-1,2-diazobenzo[e]azulene-3-carboxylic acid.

A mixture containing 5.75 g of the compound obtained in the preceding step and 60 ml of acetic acid is heated under reflux for 6 hours. After cooling, the reaction medium is poured over ice-cold water. The product formed is filtered, washed with water and dried under vacuum to give 5.07 g of the expected compound.

D) 1-(2,4-Dichlorophenyl)-1,4,5,6-tetrahydro-1,2-diazobenzo[e]azulene-3-carboxylic acid.

5 g of the ester obtained in the preceding step are placed in 75 ml of ethanol and 1.8 g of potassium hydroxide in 20.8 ml of water are added and then the mixture is heated under reflux for 1 hour. The mixture is concentrated under vacuum, the residue is taken up in ice-cold water, acidified to pH=1 by addition of 1N HCl and then the expected product is filtered. 4.5 g are obtained. m.p.=262° C.

NMR: 2.10–2.35 ppm : m : 2H; 2.60–3.25 ppm : m : 6H; 6.75 ppm : d : H; 7.10–7.45 ppm : m : 3H; 7.70 ppm : dd : 1H; 7.80–7.90 ppm : m : 2H.

Preparation 7

8-Chloro-1-(2,4-dichlorophenyl)-1,4,5,6-tetrahydro-1,2-diazabenzo[e]azulene-3-carboxylic Acid II: $g_4$=$w_2$=$w_4$=Cl, X—Y=(CH$_2$)$_3$—.

A) 5-(3-(N-Acetyl)aminophenyl)pentanoic acid.

This compound is prepared according to N. L. Allinger et al., (J. Org. Chem. 1962, 27, 70–76.

B) 2-(N-Acetyl)amino-6,7,8,9-tetrahydrobenzocyclohepten-5-one.

3.75 g of acid described in the preceding step in 20 ml of DCM are added, with vigorous stirring, to 130 g of phosphoric acid. The mixture is heated for 3 hours at 100° C. and then cooled using an ice bath and 200 ml of water are slowly added, and then the mixture is extracted with ethyl acetate and separated by settling. The organic phase is washed with water, with a 5% aqueous $Na_2CO_3$ solution and then with a saturated NaCl solution. An oil is obtained which is solidified in isopropyl ether to give 2.24 g of the expected compound, m.p.=105° C.

C) 2-Amino-6,7,8,9-tetrahydrobenzocyclohepten-5-one hydrochloride.

2.6 g of the N-acetylated derivative obtained in the preceding step are suspended in a 6N HCl solution and the mixture is heated under reflux for 2 and a half hours. The solution obtained is used as it is in the next step.

D) 2-Chloro-6,7,8,9-tetrahydrobenzocyclohepten-5-one.

The solution obtained in the preceding step is cooled to between 0° C. and 5° C. and a solution of 1.02 g of sodium nitrite in 5 ml of water is added dropwise and then kept stirring for 15 minutes. The diazoninium solution thus formed and poured over a solution of 1.22 g of CuCl in 6 ml of 6N HCl maintained at a temperature of between 0° C. and 5° C. After 1 hour at 5° C., the medium is allowed to return to RT and then 15 ml of water are added and the mixture is extracted with an ether-ethyl acetate (80/20; v/v) mixture and then concentrated under vacuum. The residue is chromatographed on silica, eluting with a toluene-ethyl acetate (95/5; v/v) mixture. 1.8 g of the expected compound are obtained in the form of a light yellow oil.

NMR: 1.60–1.95 ppm : m : 4H; 2.65–2.80 ppm : m : 2H; 2.90–3.10 ppm : m : 2H; 7.15–7.50 ppm : m : 2H; 7.65 ppm : d : 1H.

E) 8-Chloro-1-(2,4-dichlorophenyl)-1,4,5,6-tetrahydro-1,2-diazabenzo[e]azulene-3-carboxylic acid.

This compound is prepared by carrying out the procedure according to the steps described in Preparation 6.

NMR: 2.00–2.30 ppm : m : 2H; 2.55–3.25: m : 4H; 6.70 ppm : d : 1H; 7.20 ppm : d : 1H;

7.50–7.80 ppm : m : 4H; 13.1 : s : 1H.

By carrying out the procedure as described in Preparation 1 above, the following compounds are obtained:

TABLE 1

(II)

| Preparation | X—Y | g₄ | w₂ | w₄ | m.p. °C. | NMR |
|---|---|---|---|---|---|---|
| 8 | CH₂—S | F | Cl | Cl | 260 | 4.05 ppm: s: 2H; 6.55–6.65 ppm: m: 1H; 7.00–7.15 ppm: m: 1H; 7.40 ppm: d: 1H; 7.70–8.00: m: 3H. |
| 9 | CH₂—S | Br | Cl | Cl | 170 | 4.05 ppm: s: 2H; 6.50 ppm: d: 1H; 7.40 ppm: dd: 1H; 7.70–8.00 ppm: m: 4H. |
| 10 | S—CH₂ | Cl | Cl | Cl | 140 | 4.10–4.25 ppm: 2H; 6.50 ppm: d: 1H; 7.0–7.90 ppm: m: 5H. |
| 11 | CH₂—CH₂ | OMe | Cl | H | 236 | |
| 12 | CH₂—CH₂ | OMe | Cl | Cl | 248 | |
| 13 | CH₂—CH₂ | Br | Cl | Cl | 253 | |

EXAMPLE 1

N-(Piperid-1-yl)-7-chloro-1-(2,4-dichlorophenyl)-1,5-dihydroisothiochromeno[4,3-c]pyrazole-3-carboxamide, hemihydrate

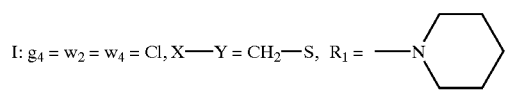

I: g₄ = w₂ = w₄ = Cl, X—Y = CH₂—S, R₁ =

A) 7-Chloro-1-(2,4-dichlorophenyl)-1,5-dihydroisothiochromeno[4,3-c]pyrazole-3-carboxylic acid chloride.

0.37 ml of thionyl chloride is added, at RT, to a mixture of 0.7 g of the compound obtained in Preparation 1 and 20 ml of toluene and then the mixture is heated under reflux for 3 hours. After cooling to RT, the reaction mixture is concentrated under vacuum, the residue is taken up in 20 ml of toluene and the solvent is evaporated under vacuum. 0.73 g of the expected product is obtained in the form of an oil which is used as it is.

B) N-(Piperid-1-yl)-7-chloro-1-(2,4-dichloro-phenyl)-1,5-dihydroisothiochromeno[4,3-c]-pyrazole-3-carboxamide, hemihydrate.

A solution of 0.2 ml of 1-aminopiperidine and 0.25 ml of triethylamine in 15 ml of DCM is cooled to 0° C., a solution of 0.73 g of the compound obtained in the preceding step in 15 ml of DCM is added dropwise and the mixture is kept stirring for 18 hours at RT. The reaction mixture is poured over 200 ml of water, extracted with DCM, the organic phase is washed with water, with a saturated NaCl solution, dried over Na₂SO₄ and the solvent is evaporated under vacuum. The residue is chromatographed on silica gel, eluting with the toluene/AcOEt mixture from (95/5; v/v) to (90/10; v/v). 0.32 g of the expected compound is obtained after crystallization from the DCM/iso ether mixture, m.p.= 148° C.

NMR: 1.2–1.8 ppm : m : 6H; 2.8 ppm : t : 4H; 4.1 ppm : s : 2H; 6.5–8.1 ppm : m : 6H; 9.4 ppm : s : 1H.

EXAMPLE 2

N-(8-azaspiro[4.5]dec-8-yl)-7-chloro-1-(2,4-dichlorophenyl)-1,5-dihydroisothiochromeno-[4,3-c]pyrazole-3-carboxamide

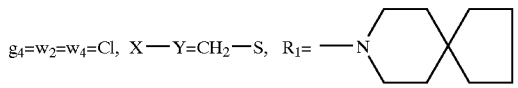

I: g₄=w₂=w₄=Cl, X—Y=CH₂—S, R₁=

A solution of 0.28 g of 8-azaspiro[4.5]dec-8-ylamine hydrochloride and 0.41 ml of triethylamine in 15 ml of DCM is cooled to 0° C., 0.6 g of the acid chloride prepared in Example 1, step A, in 10 ml of DCM is added dropwise and the mixture is left for 4 hours, with stirring, at RT. The mixture is extracted with DCM, the organic phase is washed with water, with a saturated NaCl solution, dried over Na₂SO₄ and the solvent is evaporated under vacuum. The residue is chromatographed on silica gel, eluting with the toluene/AcOEt (95/5; v/v) mixture. 0.45 g of the expected compound is obtained in amorphous form.

NMR: 1.3–1.8 ppm : m : 12H; 2.85 ppm : t : 4H; 4.05 ppm s : 2H; 6.5–8.05 ppm : m : 6H; 9.4 ppm : s : 1H.

The procedure is then carried out as described in the EXAMPLES above in order to prepare the compounds according to the invention which are presented in TABLE 2.

TABLE 2
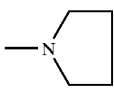
(I)
| Examples | X-Y | g₄ | w₂ | w₄ | R₁ | m.p. °C. |
|---|---|---|---|---|---|---|
| 3 | CH₂—S | Cl | Cl | Cl | 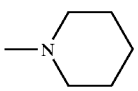 | 112 |
| 4 | CH₂—S | F | Cl | Cl |  | 248 |
| 5 | CH₂—S | F | Cl | Cl | 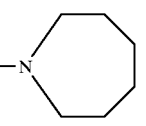 | 218 |
| 6 | CH₂—S | F | Cl | Cl | 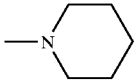 | 215 |
| 7 | CH₂—S | Br | Cl | Cl |  | 222 |
| 8 | CH₂—S | Br | Cl | Cl | 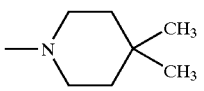 | 170 |
| 9 | CH₂—S | Br | Cl | Cl | 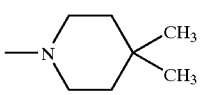 | 150 |
| 10 | CH₂—S | Cl | Cl | Cl |  | 143 |
| 11 | CH₂—S | Cl | Cl | Cl | 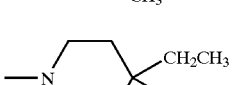 | 226 |
| 12 | CH₂—S | Cl | Cl | Cl | 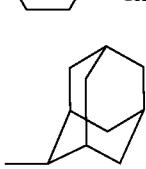 | 146 |
| 13 | CH₂—S | Cl | Cl | Cl |  | 263 |

TABLE 2-continued
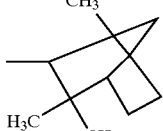
(I)
| Examples | X-Y | g$_4$ | w$_2$ | w$_4$ | R$_1$ | m.p. °C. |
|---|---|---|---|---|---|---|
| 14 | CH$_2$—S | Cl | Cl | Cl | 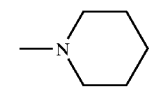 (1S)endo | 98 |
| 15 | CH$_2$S(O)$_2$ | Cl | Cl | Cl | 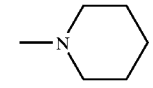 | 298 |
| 16 | CH$_2$SO | Cl | Cl | Cl | 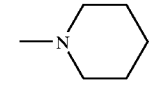 | 220 |
| 17 | S—CH$_2$ | Cl | Cl | Cl | 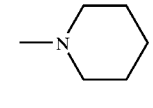 | 147 |
| 18 | CH$_2$—CH$_2$ | Cl | Cl | Cl | 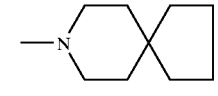 | 217 |
| 19 | CH$_2$—CH$_2$ | Cl | Cl | Cl |  | 193 |
| 20 | CH$_2$—CH$_2$ | Cl | Cl | Cl | 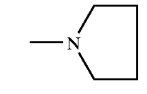 | 216 |
| 21 | CH$_2$—CH$_2$ | Cl | Cl | Cl | 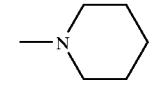 | 246 |
| 22 | CH$_2$—CH$_2$ | CF$_3$ | Cl | Cl | 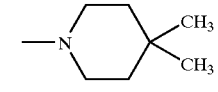 | 198 |
| 23 | CH$_2$—CH$_2$ | CF$_3$ | Cl | Cl |  | 178 |

TABLE 2-continued
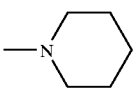
(I)
| Examples | X-Y | g₄ | w₂ | w₄ | R₁ | m.p. ° C. |
|---|---|---|---|---|---|---|
| 24 | (CH₂)₃ | H | Cl | Cl | 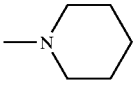 | 170 |
| 25 | (CH₂)₃ | Cl | Cl | Cl | 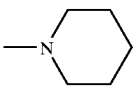 | 202 |
| 26 | CH₂—CH₂ | OMe | Cl | H | 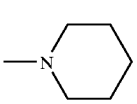 | 210 |
| 27 | CH₂—CH₂ | OMe | Cl | Cl | 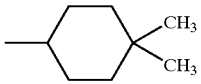 | 232 |
| 28 | CH₂—CH₂ | OMe | Cl | Cl |  | 178 |
| 29 | CH₂—CH₂ | OMe | Cl | Cl |  | 117 |
| 30 | CH₂—CH₂ | OMe | Cl | Cl | 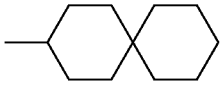 | 169 |
| 31 | CH₂—CH₂ | Br | Cl | Cl | 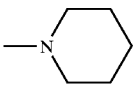 | 248 |
| 32 | CH₂—CH₂ | Br | Cl | Cl | 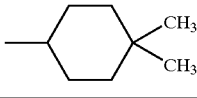 | 148 |
| 33 | CH₂—CH₂ | Br | Cl | Cl | | 211 |

What is claimed is:

1. A compound of formula:

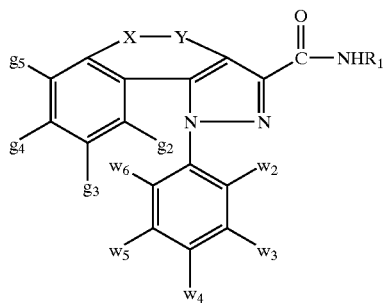

in which:

X—Y— represents —CH$_2$—S(O)$_p$— or —S(O)$_p$—CH$_2$—;

n is equal to 1 or 2;

p is equal to zero, 1 or 2;

g$_2$, g$_3$, g$_4$, g$_5$, w$_2$, w$_3$, w$_4$, w$_5$, w$_6$ are identical or different and each independently represent hydrogen, a halogen, a trifluoromethyl, a (C$_1$–C$_4$)alkyl, a (C$_1$–C$_4$)alkoxy, a (C$_1$–C$_4$)alkylthio, a nitro; at least one of the substituents w$_2$, w$_3$, w$_4$, w$_5$, w$_6$ being different from hydrogen;

R$_1$ represents an NR$_2$R$_3$ group;

R$_2$ and R$_3$ each separately represent hydrogen or a (C$_1$–C$_6$)alkyl, or R$_2$ or R$_3$, together with the nitrogen atom to which they are attached, constitute a saturated or unsaturated 5- to 10-membered heterocyclic radical which is unsubstituted or substituted one or several times with a (C$_1$–C$_4$)alkyl;

or a pharmaceutically acceptable salt or solvate thereof.

2. The compound as claimed in claim 1, in which g$_2$, g$_3$, g$_5$, w$_3$, w$_5$, w$_6$ represent hydrogen and g$_4$, w$_2$ and w$_4$ have one of the values defined above for the compounds of formula (I) except hydrogen.

3. The compound as claimed in claim 2, in which w$_2$ and w$_4$ represent chlorine and g$_4$ represents chlorine or bromine.

4. A compound as claimed in claim 3, in which R$_1$ represents NR$_2$R$_3$, R$_2$ and R$_3$ constituting, with the nitrogen atom to which they are attached, a saturated 5- to 10-membered heterocyclic radical which is unsubstituted or substituted one or several times with a (C$_1$–C$_4$)alkyl.

5. A compound as claimed claim 4, in which X—Y represents —CH$_2$—S—.

6. A pharmaceutical composition containing a compound as claimed in claim 1.

7. The pharmaceutical composition as claimed in claim 6, in the form of a dosage unit.

8. A pharmaceutical composition containing a compound as claimed in claim 2.

9. A pharmaceutical composition containing a compound as claimed in claim 3.

10. A pharmaceutical composition containing a compound as claimed in claim 4.

11. A pharmaceutical composition containing a compound as claimed in claim 5.

* * * * *

UNITED STATES PATENT AND TRADEMARK OFFICE
CERTIFICATE OF CORRECTION

PATENT NO.       : 6,906,080 B1
APPLICATION NO.  : 10/111765
DATED            : June 14, 2005
INVENTOR(S)      : Barth et al.

It is certified that error appears in the above-identified patent and that said Letters Patent is hereby corrected as shown below:

Column 13, line 9: 1H-4x6-isothiochromeno-[4,3-c]pyrazole-3-carboxylic" should read as -- 1H-4$\lambda^6$-isothiochromeno-[4,3-]pyrazole-3-carboxylic --.

Column 17, lines 16 to 29: In Formula (II), "$w_1$" should read as -- $w_4$ --.

Column 19, line 3: In Formula (I), "$w_1$" should read as -- $w_4$ --.

Column 21, line 3: In Formula (I), "$w_1$" should read as -- $w_4$ --.

Column 23, line 3: In Formula (I), "$w_1$" should read as -- $w_4$ --.

Signed and Sealed this

Twenty-second Day of August, 2006

JON W. DUDAS
*Director of the United States Patent and Trademark Office*